United States Patent
Orth et al.

(10) Patent No.: US 7,801,632 B2
(45) Date of Patent: Sep. 21, 2010

(54) METHOD OF DESIGNING THE SURFACE OF A DENTAL PROSTHETIC ITEM CONSISTING OF THREE DIMENSIONAL DATA

(75) Inventors: Ulrich Orth, Lautertal (DE); Volker Wedler, Hirschberg (DE); Ulf Willers, Darmstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 389 days.

(21) Appl. No.: 11/175,253

(22) Filed: Jul. 7, 2005

(65) Prior Publication Data

US 2006/0008776 A1 Jan. 12, 2006

(30) Foreign Application Priority Data

Jul. 8, 2004 (DE) .................. 10 2004 038 136

(51) Int. Cl.
*A61C 5/00* (2006.01)
(52) U.S. Cl. .......................... 700/98; 433/215
(58) Field of Classification Search .......... 433/215, 433/223, 213, 202.1, 204; 700/97–98
See application file for complete search history.

(56) References Cited

U.S. PATENT DOCUMENTS

| | | | | |
|---|---|---|---|---|
| 4,937,928 A | * | 7/1990 | van der Zel | 29/896.1 |
| 5,691,905 A | * | 11/1997 | Dehoff et al. | 700/98 |
| 6,174,168 B1 | | 1/2001 | Dehoff et al. | |
| 6,821,462 B2 | * | 11/2004 | Schulman et al. | 264/16 |
| 7,086,863 B2 | * | 8/2006 | Van der Zel | 433/223 |
| 7,399,181 B2 | * | 7/2008 | Weber et al. | 433/29 |
| 2006/0063135 A1 | * | 3/2006 | Mehl | 433/223 |

FOREIGN PATENT DOCUMENTS

| | | |
|---|---|---|
| EP | 1 252 867 | 10/2002 |
| EP | WO 2004/044787 A2 | 5/2004 |

* cited by examiner

*Primary Examiner*—Cris L Rodriguez
*Assistant Examiner*—Hao D Mai
(74) *Attorney, Agent, or Firm*—Fitzpatrick, Cella, Harper & Scinto

(57) ABSTRACT

A method and apparatus for designing the surface of a dental prosthetic item consisting of three-dimensional data, wherein three-dimensional data of a surface (30) of an electronically stored tooth (11) are used at least as part of the surface of the dental prosthetic item to be fabricated, to which end the surface of the tooth (30) is first of all determined as to size and then placed against an electronically stored prosthetic item or the region of a preparation site (1;21) existing as three-dimensional data. The position of the digital tooth surface (30) over the dental prosthetic item or in the preparation site (1; 21) can be set with regard to at least one spatial axis and/or at least one direction of rotation.

10 Claims, 5 Drawing Sheets

METHOD OF DESIGNING THE SURFACE OF A DENTAL PROSTHETIC ITEM CONSISTING OF THREE DIMENSIONAL DATA

The invention relates to a method for designing the surface of a dental prosthetic item consisting of three dimensional data.

In order to fabricate esthetic and functional tooth restorations, it is necessary to produce a direct copy or a mirror image copy of one or more tooth surfaces. The labial surfaces of the anterior teeth should be symmetrical in order to achieve an overall esthetic appearance. In the region of the lateral teeth, the occlusion surface of the corresponding tooth on the opposite side of the mouth forms a suitable template for the chewing surface of the restoration.

DESCRIPTION OF THE RELATED ART

In the design methods used hitherto, the tooth surface as it was prior to preparation or an artificial waxed-up surface can be transferred to the surface of the restoration. For this purpose, some of the three dimensional data are copied.

During the manual fabrication process, the dental technician, when working on an anterior tooth, attempts to achieve the best possible resemblance to the contralateral tooth. This can be achieved more or less successfully, but never exactly. In the region of the lateral teeth, the dental technologist concentrates on dentition morphology, including that of the lateral tooth. Determining and imitating important features, however, depends on the manual dexterity of the dental technician.

SUMMARY AND OBJECTS OF THE INVENTION

The method of the invention for designing the surface of a dental prosthetic item using three dimensional surface data of a tooth surface is based on using any given tooth surface of an electronically stored tooth at least as part of the surface of the prosthetic item to be fabricated, for which purpose the dimensions of the tooth surface will be set and then matched against an electronically stored prosthetic item or placed in the region of a preparation site existing in the form of three dimensional data. In doing so, the position of the digital tooth surface on the dental prosthetic item or in the preparation site can be set in regard to at least one spatial axis and/or at least one direction of rotation.

The dental prosthetic item exists as digital data and is depicted in such a manner that it can be implemented by CAD tools. This makes it possible to form a detailed design of elevations and depressions on the dental prosthetic item and thus give it a more natural appearance.

The tooth is itself available in the form of three dimensional data, although it may be sufficient to provide access to only parts of the tooth.

In cases in which no prosthetic item has yet been designed, the tooth surface is placed against the preparation site itself, in the manner described in the exemplary embodiment. This, therefore, does not involve providing a dental prosthetic item already existing as a 3D data set with a new surface, but rather the design of a prosthetic item based on the orientation of the tooth surface relative to the preparation site, by making use of the data relating to the preparation site and those relating to the tooth surface. The latter is explained in the exemplary embodiment.

The borders of the tooth surface to be inserted are advantageously computed to fit the surface of the dental prosthetic item or the preparation site. A smooth transition of the surfaces relative to each other is achieved through interpolation between the tooth surface and the surface of the prosthetic item.

According to an advantageous development of the invention, the position of the digital tooth surface on the dental prosthetic item or in the preparation site can be arbitrarily defined. Free alignment is thus possible without computational correlation of the data establishing a forced position.

If the digital tooth surface is mirror-inverted before insertion thereof and an original surface is not available, it will then be possible to have recourse to a surface which is axially symmetrical.

A surface to be inserted that has been created from a contralateral tooth is particularly well suited for this purpose. In the case of a tooth in the anterior region, it is possible to use the visible anterior surface.

In the case of a tooth in the buccal region, a mirror image of the chewing surface of the contralateral tooth can be advantageously used.

Prior to computational adjustment using the existing digital tooth structure, a size adjustment of the surface to be inserted is advantageously carried out relative to the appropriate dimensions for the prosthetic item or preparation site. This makes it possible to use teeth from tooth libraries as a template for a tooth surface.

This procedure is especially advantageous for designing a veneer.

A digital dental prosthetic item designed according to the invention can then be used for fabricating a physical dental prosthetic item using standard dental machining equipment.

The invention further relates to a device for designing the surface of a dental prosthetic item in the form of three dimensional data, for which device means are provided for selecting the three dimensional data of a tooth surface of an electronically stored tooth consisting of at least part of the surface of the dental prosthetic item to be designed, and for positioning the said tooth surface against an electronically stored dental prosthetic item or in a region of a preparation site available in the form of three dimensional data, and that additional means are provided for adjusting the selected part of the tooth surface at least relatively to the orientation of the dental prosthetic item or to the preparation site.

The means for adjusting the selected part of the tooth surface are advantageously provided with regard to at least one of the properties of size and margin profile.

Moreover, means can be provided for computational adjustment of the borders of the tooth surface to be inserted relative to the surface of the dental prosthetic item.

It is particularly advantageous if means are provided for mirror-imaging the tooth surfaces to be inserted.

BRIEF DESCRIPTION OF THE DRAWINGS

The method of the invention is explained below with reference to the drawings, in which.

DETAILED DESCRIPTION OF EXEMPLARY EMBODIMENT(S) OF THE INVENTION

The method of the invention will now be described with reference to the fabrication of a veneer by way of example. CAD software for creating dental prosthetic items, in the design mode, makes it possible to copy and, if required, to form mirror images of any tooth surface on a dental prosthetic item, also referred to as a restoration item. The user can merge the "shell" of the copied surface with the restoration item by using the following functions: positioning, rotation, size adjustment and, when necessary, machining. In this manner, existing tooth designs can also be transferred for fitting to the surface with little effort.

Figure 1:
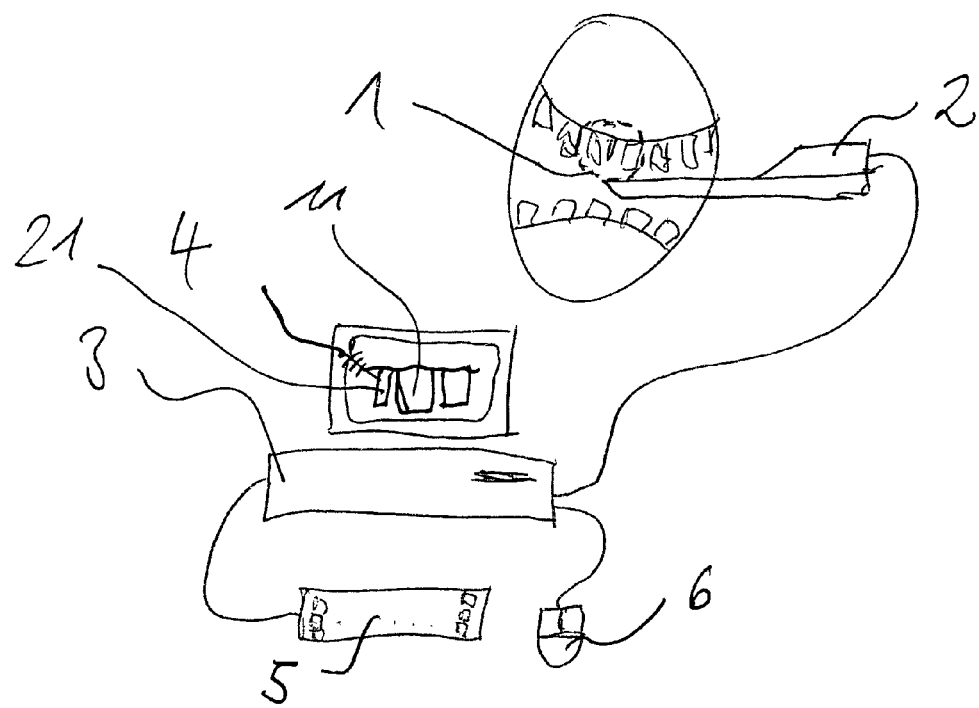
FIG. 1 illustrates scanning of a preparation site using an intra-oral camera

In a first step, illustrated in FIG. 1, the preparation site 1 is scanned with an intra-oral camera 2, and a three dimensional data set of the preparation site 1 is generated with the help of the scanned data evaluated by a computer 3 and displayed on a display unit 4, in this example for a front tooth 21 to be restored. Moreover, input devices in the form of a keyboard 5 and a computer mouse 6 are provided.

In the present case it is advisable to extend scanning over a wider area than just the preparation site. This can be accomplished, for example, by additionally scanning the adjacent teeth 11. The image of tooth 21 was taken from the labial direction.

The tooth surface to be used for the fabrication of the restoration is scanned to give an additional image. Typically, this is done from the same perspective as the preparation site image.

Figure 2A:
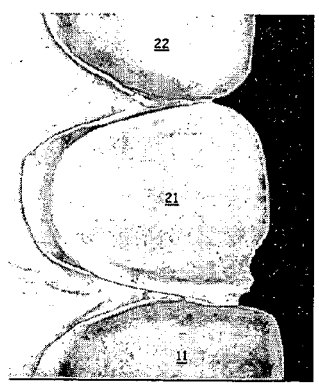
FIGS. 2A to 2C show digitized depictions of a tooth to be restored, the adjacent teeth and a template tooth in the region of the anterior teeth.
Figure 2B:
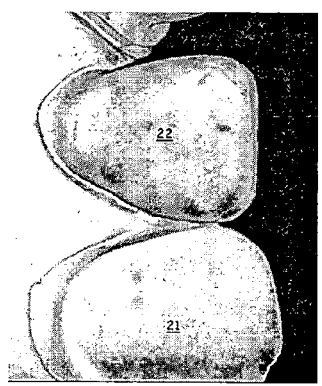
Figure 2C:
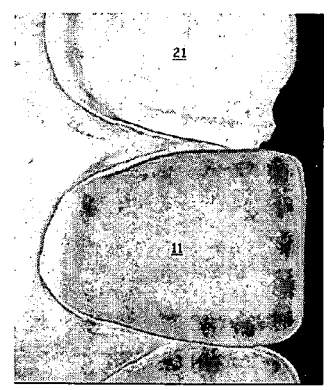

In the present case, it is sufficient to use the preparation in the zone of the front tooth 21 to be replaced as well as the adjacent teeth 11 and 22, as the tooth surface of tooth 11, which will be used as the surface of the restoration, is also displayed in these images shown in FIGS. 2A, 2B, and 2C, but this applies only to the region of the inner front teeth. For teeth located further away, many camera images would be necessary in order to carry out this procedure. In this case, the prepared tooth with its adjacent teeth is advantageously displayed in a series of images, and the tooth surface to be copied is advantageously displayed in another series of images.

Figure 3:
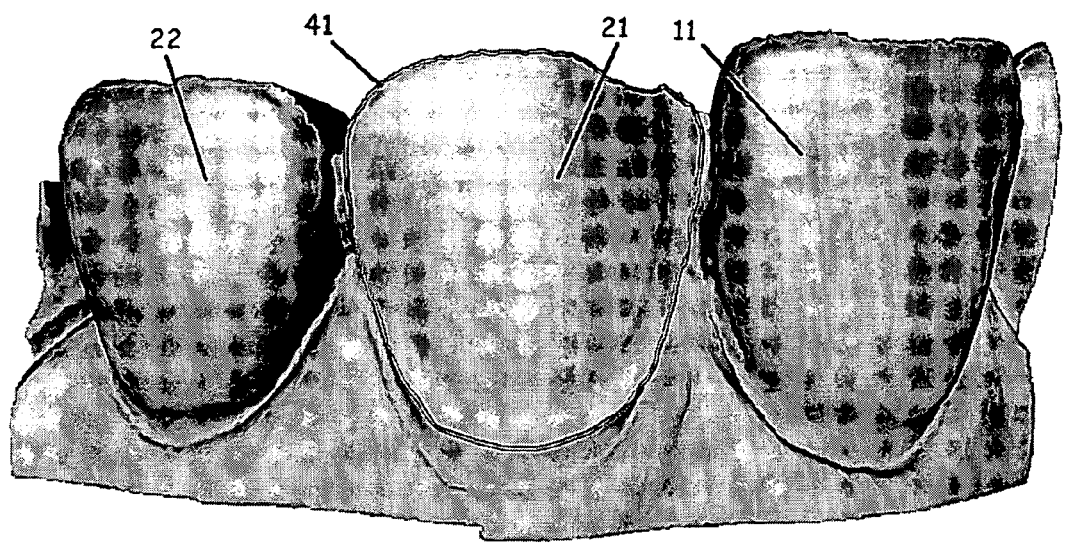
FIG. 3 shows the drawn preparation margin.

The process of drawing the preparation margin 41 of the front tooth 21 to be restored is shown in FIG. 3. This is done using a computer mouse 6, but it can also be done using a light pen or some other input device. Means allowing the preparation margin 41 to be automatically recognized may be provided, if desired.

Figure 4:
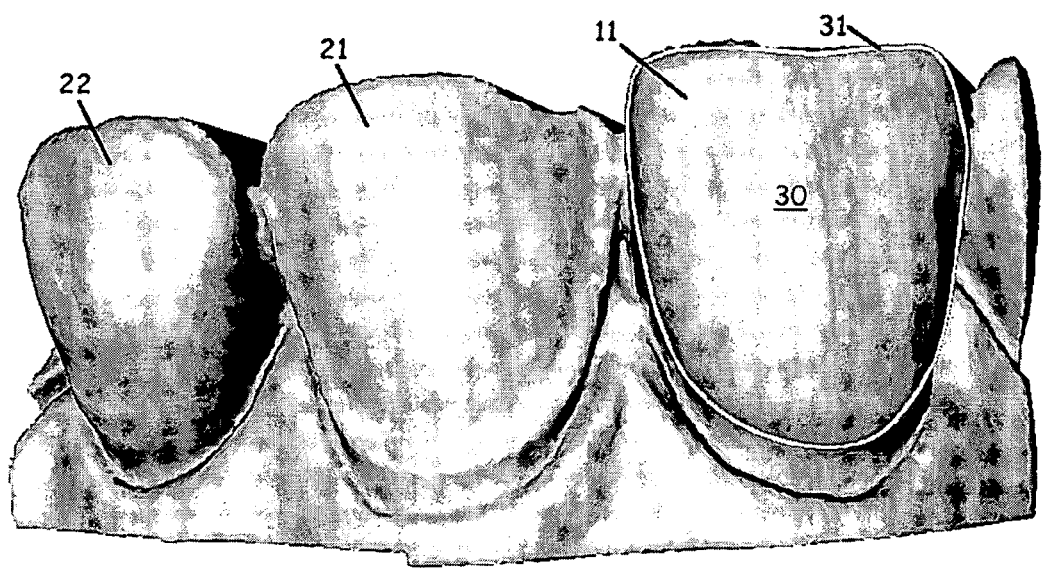
FIG. 4 shows the selection of a tooth surface to be copied from an anterior tooth contralateral to the tooth to be repaired.

A tooth surface 30 to be copied is selected from the contralateral front tooth 11 by defining a borderline 31 using said input devices (see FIG. 4). The selection of surface 30 can be checked by imaging front tooth 11 from different directions.

To transfer the selected tooth surface 30 of front tooth 11 onto front tooth 21 to be restored, it is necessary to form a mirror image of the selected tooth surface 30, for which purpose a dialog box is shown.

In cases in which no occlusion images have been generated, it is not necessary to enquire whether the selected surface should be mirror-inverted, as in this case only the contralateral tooth can be used and therefore it is already known that mirror-inversion is required.

Figure 5:
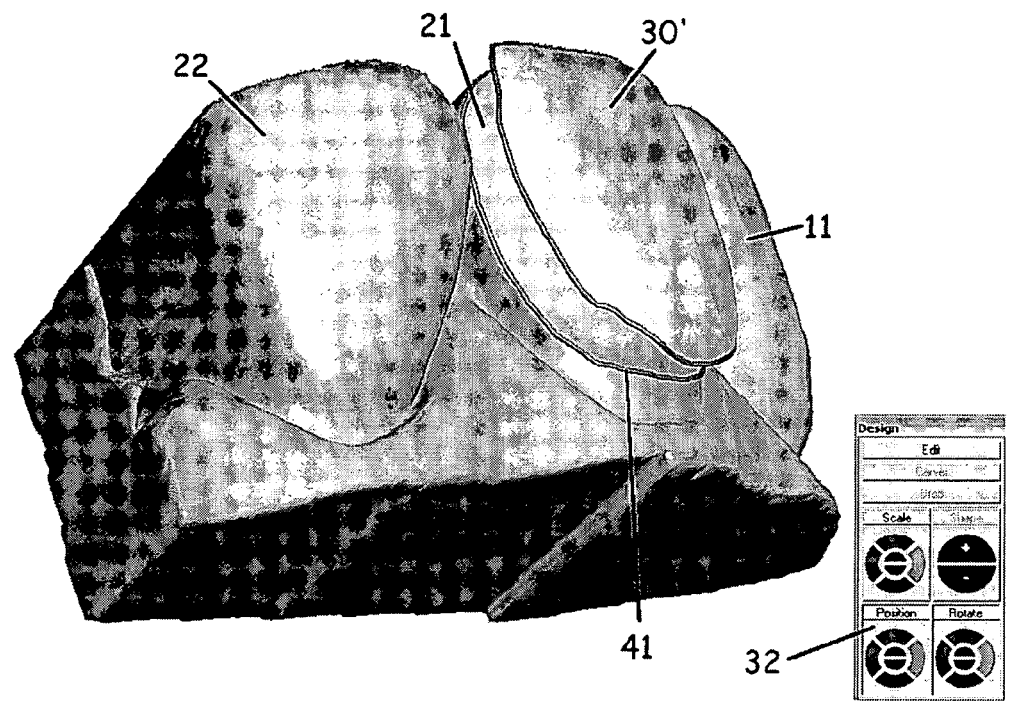
FIG. 5 illustrates positioning of the mirror-inverted tooth surface over the tooth to be restored within the preparation site.

After tooth surface 30 has been mirror-inverted such that a right hand surface is depicted as a left hand surface, the mirror-inverted tooth surface 30 is merged with preparation site 1 where it can be positioned over tooth 21 by input means 32 in the form of, say, programmed pushbuttons, in other words, it can be moved and rotated in all spatial directions (see FIG. 5). Moreover, its size can be altered, so that adjustment thereof to match adjacent tooth 22 is possible.

Figure 6:
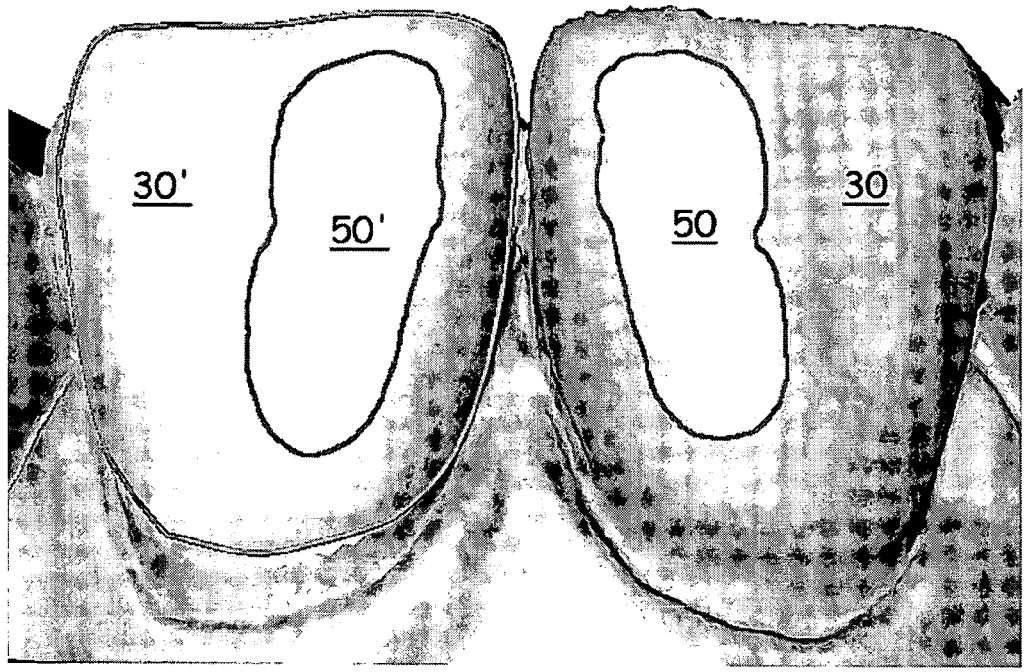
FIG. 6 illustrates the tooth surface used as a template and having worked-in light reflective surfaces.

In this exemplary embodiment, light reflective surfaces are worked into tooth surface 30 used as a template, which reflective surfaces can be identified, for example, as a coherent zone 50, as illustrated in FIG. 6. This zone 50 can also be duplicated in the copied tooth surface 30 as zone 50, thereby making it possible to adjust both zones 50, 50 to each other in terms of their horizontal and vertical positions and their angle of tilt, as well as in their dimensions, ie, their size.

Figure 7:
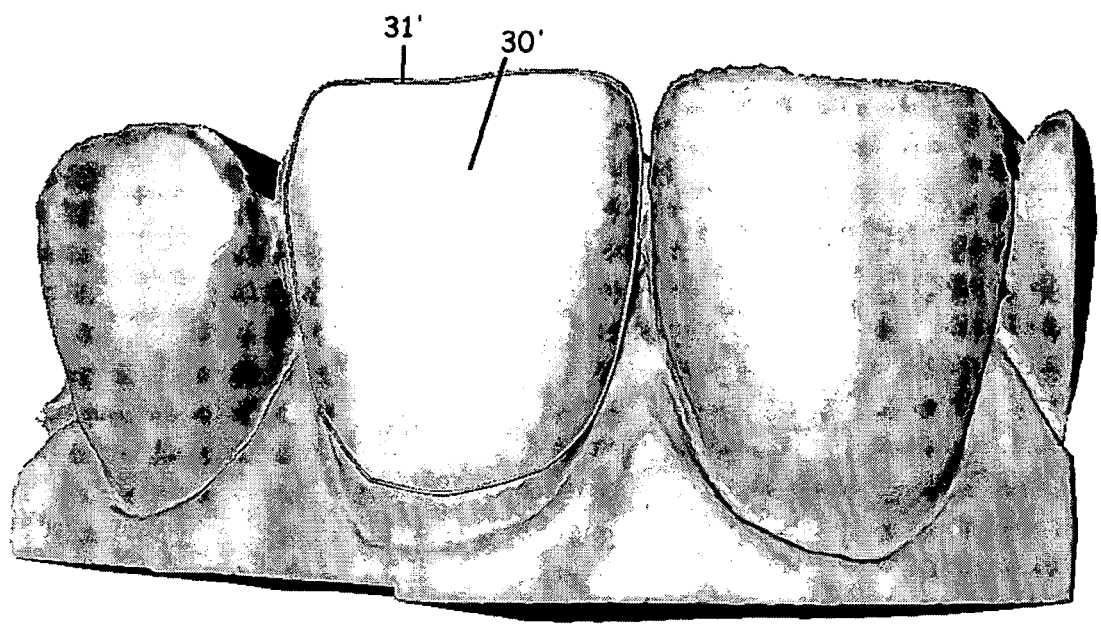
FIG. 7 shows the inserted copied surface in its final position prior to adjustment of the margin of the copied surface.

In FIG. 7, the inserted surface 30 is illustrated in its final position on the computed dental prosthetic item, so that it is possible to adjust margin 31 of surface 30 while observing the preparation border.

Figure 8A:
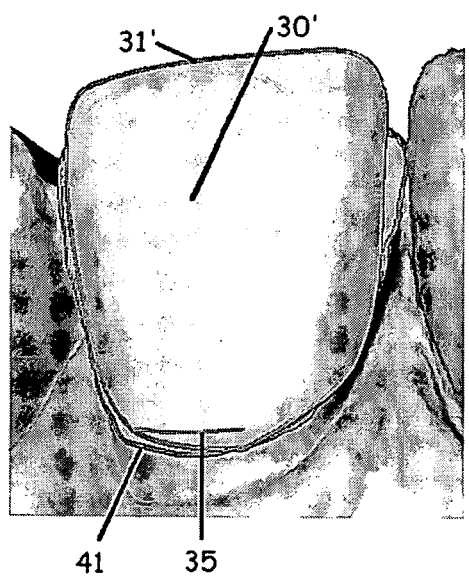
FIGS. 8A and 8B illustrate positioning of the margin of the copied surface relative to the designed dental prosthetic item.
Figure 8B:
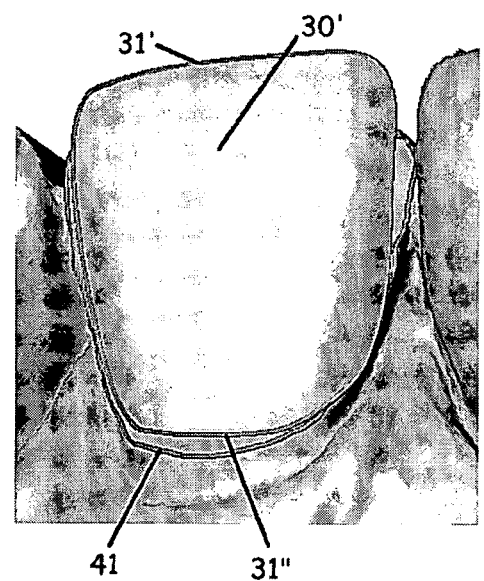

This is accomplished using standard machining tools, see FIGS. 8A and 8B, in which margin 31 of copied surface 30 is altered by redrawing a line section 35. In this manner copied surface 30 is reduced or enlarged locally. Preparation border 41 is displayed for checking purposes.

After this adjustment, the next step comprises pictorially merging the designed surface 30 with preparation 21, by which means the required dental prosthetic item is formed. In doing so, the surfaces of preparation 21 are used for forming the dental prosthetic item surface near the preparation and then a computed enhancement is generated to provide a preliminary data set for a dental prosthetic item to be later revised.

Figure 9A:
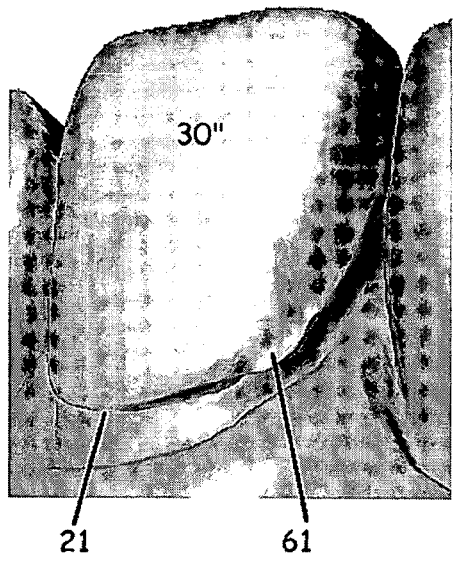
FIGS. 9A and 9B illustrate merging and correction of the copied surface with the designed dental prosthetic item.
Figure 9B:
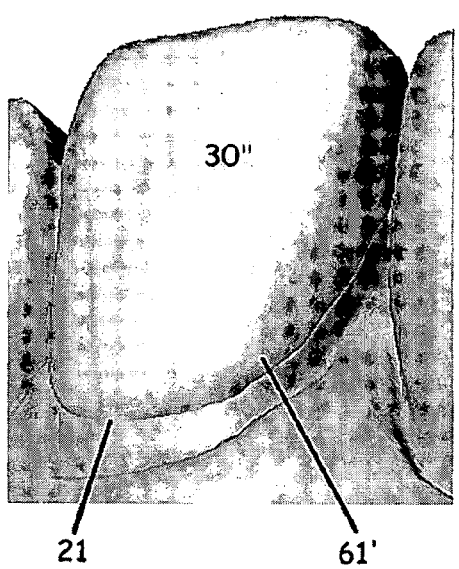

A displayed proposal for connecting the dental prosthetic item to preparation 21 is illustrated in FIG. 9A. This proposed connection can be adjusted so as to make the transition regions 61 fit. Changes may be necessary in all or only part of the zone between surface 30 and preparation 21. The result of this adjustment is illustrated in FIG. 9B, where the transition region 61 is considerably smoother.

Figure 10A:
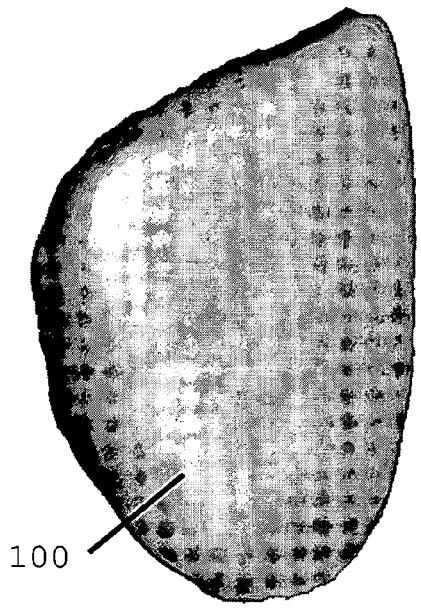
FIG. 10A is a front view of the finished designed dental prosthetic item.
Figure 10B:
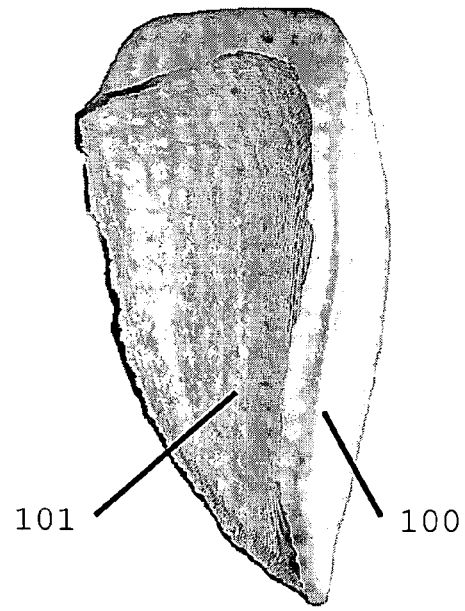
FIG. 10B is a rear view of the finished designed dental prosthetic item of FIG. 10A

The finished designed dental prosthetic item in the form of a veneer 100 is illustrated in FIG. 10A as viewed from the labial direction, and the rear side 101 of the dental prosthetic item is illustrated in FIG. 10B as viewed from the buccal direction. The dental prosthetic item is fastened to the front tooth via this rear side 101.

Designing a crown requires an image from the occlusal direction and knowledge of the occlusal surface, which can also be obtained by copying, after which the region extending from the occlusal surface to the preparation border is completed. The outer contours of the dental prosthetic item to be fabricated are determined in this manner, and the inner contours are defined by the existing tooth stump, thereby determining the shape of the dental prosthetic item in its entirety. This designed dental prosthetic item can then be fabricated by standard procedures.

Using this designing procedure, the user is able to make either a direct copy or a mirror image copy of any tooth surface, even a self-defined one such as the labial surface of front teeth or the chewing surface of lateral teeth, and use the copy as the surface for a restoration.

In doing so, the user can use the original surface of the tooth prior to preparation, while, unlike the known correlation procedures, the position of the tooth surface can be freely selected and false positions can thus be corrected while retaining the surface details.

Moreover, the contralateral tooth can be used as the surface for the restoration. In this manner, the user can achieve the greatest possible symmetry, especially in the region of the anterior teeth. In the region of the lateral teeth, the chewing surface of the contralateral tooth is the appropriate template for the restoration, as this chewing surface fits in best with the other teeth in the jaw and therefore also with the teeth in the opposite jaw.

Furthermore, it is possible to use any templates to achieve the greatest possible symmetry, eg, in the restoration of the entire front teeth region, even if the original tooth surfaces are not used.

Thus, for example, the front tooth on the right-hand side can be provided directly with a template, and the front tooth on the left-hand side with a mirror image template, and any necessary size adjustment can be made by scaling the copied surfaces.

Using this method it is possible, for the first time, to create, without great manual or artistic effort, esthetic and functional restorations that meet all symmetry-related requirements, especially in the region of the anterior teeth.

The invention claimed is:

1. A method of designing the surface of a single dental prosthetic construct consisting of three-dimensional data, wherein three-dimensional data corresponding to a portion of a surface of an electronically stored tooth are used at least as part of the surface of the dental prosthetic construct to be fabricated, the method comprising the steps of:
    selecting the three-dimensional data to be used by identifying a desired portion of the surface of the electronically stored tooth;
    placing the selected three-dimensional data against a region of a preparation site existing in computer-readable memory as three-dimensional data;
    setting the position of selected three-dimensional data in the preparation site in at least one spatial axis and at least one direction of rotation; and
    adjusting borders of selected three-dimensional data by computer computation with reference to said preparation site,
    wherein the dental prosthetic construct is for a tooth to be restored and the electronically stored tooth exists in computer-readable memory and represents an image of an existing tooth in the mouth of the patient for whom the dental prosthetic construct is being designed that is different from the tooth to be restored.

2. A method as defined in claim 1, wherein the position of the selected three-dimensional data in the preparation site can be freely set with regard to the axes in at least one of space and directions of rotation.

3. A method as defined in claim 1, wherein the selected three-dimensional data are minor-inverted prior to placement against the region of the preparation site.

4. A method as defined in claim 1, wherein the selected three-dimensional data are obtained from an electronically stored contralateral tooth.

5. A method as defined in claim 1, wherein the occlusal surface of a contralateral tooth in the region of the lateral teeth is used in mirror-inverted form.

6. A method as defined in claim 1, wherein the selected three-dimensional data are adjusted as to size.

7. A method as defined in claim 1, wherein a veneer is designed.

8. A device for designing the surface of a single dental prosthetic construct consisting of three-dimensional data, wherein three-dimensional data corresponding to a portion of a surface of an electronically stored tooth are used at least as part of the surface of the dental prosthetic construct to be fabricated, the device comprising:
    means for selecting the three-dimensional data to be used by identifying a desired portion of the surface of the electronically stored tooth;
    means for placing the selected three-dimensional data against a region of a preparation site existing as three-dimensional data;
    means for adjusting the selected three-dimensional data at least as regards its orientation relative to said preparation site; and
    means for computational adaptation of the boundaries of the selected three-dimensional data with reference to said preparation site,
    wherein the dental prosthetic construct is for a tooth to be restored and the electronically stored tooth exists in computer-readable memory and represents an image of an existing tooth in the mouth of the patient for whom the dental prosthetic construct is being designed that is different from the tooth to be restored.

9. A device as defined in claim 8, wherein means are provided for adapting the selected three-dimensional data at least with reference to one of the properties size and margin profile.

10. A device as defined in claim 8, further comprising means for mirror-inverting said tooth surface to be inserted.

* * * * *